(12) United States Patent
Knight et al.

(10) Patent No.: US 6,575,985 B2
(45) Date of Patent: Jun. 10, 2003

(54) VESSEL EVERSION INSTRUMENT WITH CONICAL HOLDER

(75) Inventors: Gary W. Knight, West Chester, OH (US); Dale R. Schulze, Lebanon, OH (US)

(73) Assignee: Ethicon, Inc., Somerville, NJ (US)

( * ) Notice: Subject to any disclaimer, the term of this patent is extended or adjusted under 35 U.S.C. 154(b) by 56 days.

(21) Appl. No.: 09/949,601

(22) Filed: Sep. 10, 2001

(65) Prior Publication Data

US 2003/0050651 A1 Mar. 13, 2003

(51) Int. Cl.$^7$ ................................................ A61B 17/04
(52) U.S. Cl. ...................................................... 606/149
(58) Field of Search ................................ 606/149, 150, 606/153, 151, 155; 227/19

(56) References Cited

U.S. PATENT DOCUMENTS

| 2,086,371 | A | 7/1937 | Tear |
| 2,940,452 | A | 6/1960 | Smialowski |
| 3,040,748 | A | 6/1962 | Klein et al. |
| 3,057,355 | A | 10/1962 | Smialowski et al. |
| 3,180,337 | A | 4/1965 | Smialowski |
| 3,908,662 | A | 9/1975 | Razgulov et al. |
| 4,470,415 | A | 9/1984 | Wozniak |
| 4,622,970 | A | 11/1986 | Wozniak |
| 5,261,920 | A | * 11/1993 | Main et al. ................. 606/153 |
| 6,402,764 | B1 | * 6/2002 | Hendricksen et al. ....... 606/149 |
| 2002/0173802 | A1 | * 11/2002 | Schulze ....................... 606/49 |

* cited by examiner

*Primary Examiner*—Gary Jackson
*Assistant Examiner*—Gwen Phanijphand (57) ABSTRACT

An instrument is provided for everting an end of a vessel over an end of a tubular workpiece, wherein a portion of the vessel is positioned within an axial bore of the tubular workpiece. The instrument comprises a conical holder comprising a first end, a second end, a longitudinal axis, and a lumen therethrough. The conical holder is positionable coaxially with the axial bore of the tubular workpiece. The lumen at the first end has a first diameter smaller than the diameter of the end of the tubular workpiece when extended distal to the end of the tubular workpiece. The first end is radially expandable so that the lumen at the first end is larger than the end of the tubular workpiece. The instrument further comprises a mandrel having a first end, a second end, and a longitudinal axis therebetween. The first end of the mandrel is insertable into the first end of the conical holder. The mandrel is tapered from a smaller diameter at said distal end to a larger diameter at said proximal end. The instrument further comprises a sleeve having an axial sleeve bore for slidably retaining the mandrel in coaxial alignment with the longitudinal axis of the conical holder. The sleeve has an annular groove for pressing against the first end of the conical holder with the vessel therebetween.

19 Claims, 6 Drawing Sheets

VESSEL EVERSION INSTRUMENT WITH CONICAL HOLDER

FIELD OF THE INVENTION

The field of art to which this invention relates is medical devices, more specifically, medical devices and surgical procedures for performing anastomosis of hollow organs such as blood vessels.

BACKGROUND OF THE INVENTION

Anastomosis surgical procedures are common in the field of cardiac surgery. These procedures are conventionally used for repairing a damaged or diseased blood vessel. In a typical anastomosis procedure, a surgeon joins a first blood vessel to a second blood vessel and creates a passageway between the two blood vessels to provide for the communication of blood flow. For this kind of anastomosis, the surgeon typically uses specialized grasping tools to manipulate a tiny, curved needle attached to an extremely fine surgical filament (under 0.001 inch diameter) to suture the vessels together. The vessels may be joined end-to-end, end-to-side, or side-to-side. To facilitate healing of the joined vessels, the prevailing standard of care requires that the surgeon suture the inside surfaces of the first and second vessels together, intima to intima. The surgeon must take great care not to damage the intima of each vessel so that endothelial cells may form over the anastomosis without the formation of thrombus or other complications, thus improving the likelihood of a long term patency of the vessels. For life-saving procedures such as coronary artery bypass graft surgery (CABG), this is especially important. When performing a distal anastomosis in a conventional CABG procedure, the surgeon typically sutures an end-to-side anastomosis of a distal end of a graft vessel (such as a segment of saphenous vein harvested from the patient) to a side of a target vessel (the stenosed coronary artery). For a proximal anastomosis in a conventional CABG procedure, the surgeon sutures a proximal end of the graft vessel to the side of the aorta As this field of art has progressed over the last several years, new anastomotic methods have been developed and introduced in attempts to replace the suturing technique briefly described above. Many of these methods incorporate novel fasteners and fastener appliers. The requirement, however, to maintain intima-to-intima contact of the joined vessels remains just as important with these approaches. In fact it is often necessary, prior to joining the vessels, for the surgeon to evert (i.e., turn inside out) the end of at least one of the vessels over the end of a member such as a tube, ferrule, or bushing, etc., which is a component of the fastener or fastener applier. This exposes the intima of that vessel for presentation to the intima of the other vessel prior to fastening the vessels.

Although it is possible to evert larger vessels (over 5 mm in diameter) using standard forceps and graspers available in the operating room, such methods are slow and may result in excessive damage to the vessel everted. And, often the surgeon requires assistance in performing the eversion procedure. Furthermore, vessels smaller than 5 mm are very difficult, if not impossible, to evert using such methods.

There are several requirements for an effective vessel eversion device. As noted earlier, for proper healing, it is important not to injure the intima of either vessel during the eversion procedure. The eversion device also must be easy for the surgeon to use without assistance and require only a few steps to operate. The eversion device must be useful for a wide range of blood vessel sizes, particularly small vessels, e.g., having a diameter of about 2–3 mm or less. In addition, it is desirable for the eversion device to be useful on one end of a vessel, when the opposite end is already attached to the patient (e.g., at the distal anastomosis of a patient undergoing a CABG procedure). The eversion device should also allow for the proper length of everted tissue, depending on the requirements of the anastomosis device or method to be used. Finally, it is desirable that the eversion device is low cost and yet operates reliably.

Accordingly, there is a need in this art for novel devices and methods for engaging and everting the end of a blood vessel (or other tubular body organ), which can be used in a quick and effective manner without causing trauma to the vessel or the intima of the vessel (or tubular body organ).

SUMMARY OF THE INVENTION

It is an object of the present invention to provide novel eversion devices which are easy for the surgeon to use without assistance, and which efficiently and effectively engage blood vessels and evert the ends of blood vessels, including blood vessels having small or fine diameters.

A further object of the present invention is to provide novel eversion devices which engage blood vessels and evert the ends of blood vessels without causing trauma to the blood vessel or the intima of the blood vessels.

It is yet another object of the present invention to provide novel methods of engaging and everting blood vessels quickly and efficiently, while preventing or minimizing damage to the blood vessels and the intimas of the blood vessels.

It is still yet a further object of the present invention to provide a novel vessel eversion device and procedure for everting one end of a vessel having the other end already attached to another vessel.

Accordingly, an eversion instrument for everting an end of a vessel is disclosed. The instrument has a conical holder member having a first end, a second end, a longitudinal axis, and a lumen therethrough. The conical holder member is positionable coaxially with a tubular member. The tubular member comprises an axial bore, a proximal end, a distal end and an outer surface. The distal end of the tubular member has a diameter. The lumen of the conical holder member at the first end has a first diameter smaller than the diameter of the distal end of the tubular member when positioned distal to the distal end of the tubular member. The first end of the conical member is radially expandable so that the lumen at the first end can have an expanded diameter larger than the diameter of the distal end of the tubular member. There is also a mandrel. The mandrel has a first end, a second end, and a longitudinal axis therebetween. The first end of the mandrel is insertable into the first end of the conical holder member. The mandrel is tapered from a smaller diameter at said distal end to a larger diameter at said proximal end. There is also a sleeve having an axial sleeve bore for slidably retaining the mandrel in coaxial alignment with the longitudinal axis of the conical holder. The sleeve has a distal end, and, the distal end has an annular groove for pressing against the first end of the conical holder member with a section of vessel located therebetween.

Another aspect of the present invention is the combination of a tubular member with the above-described instrument. The tubular member has a distal end, a proximal end, an axial bore and an outer surface.

Still yet another aspect of the present invention is a method of using the above-described instrument to evert the end of a vessel.

These and other aspects and advantages of the instruments and methods of the present invention will become more apparent from the following description and accompanying drawings.

DETAILED DESCRIPTION OF THE INVENTION

Figure 1:
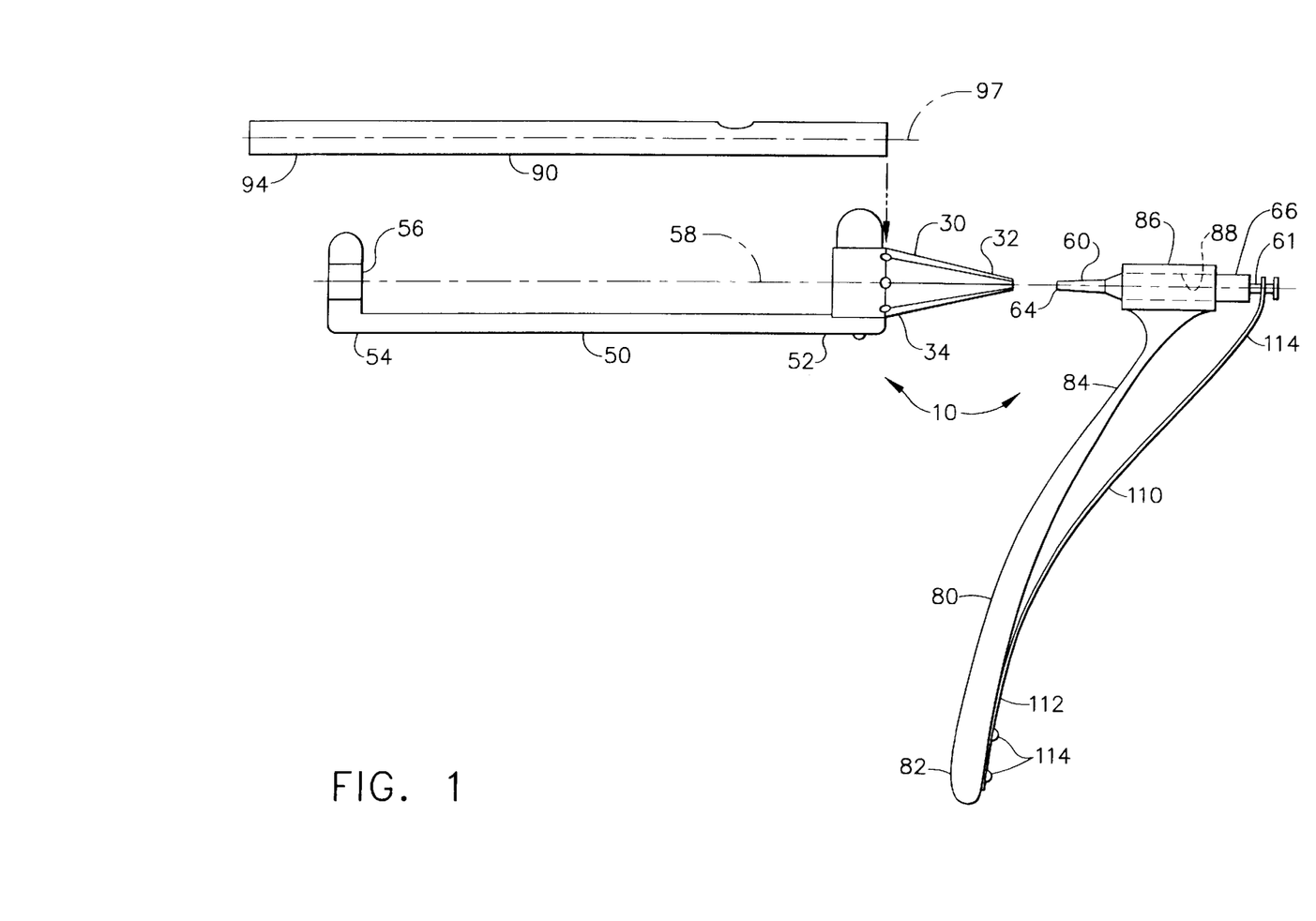
FIG. 1 is a side view of an eversion instrument 10 of the present invention and a tubular workpiece 90.
Figure 2:
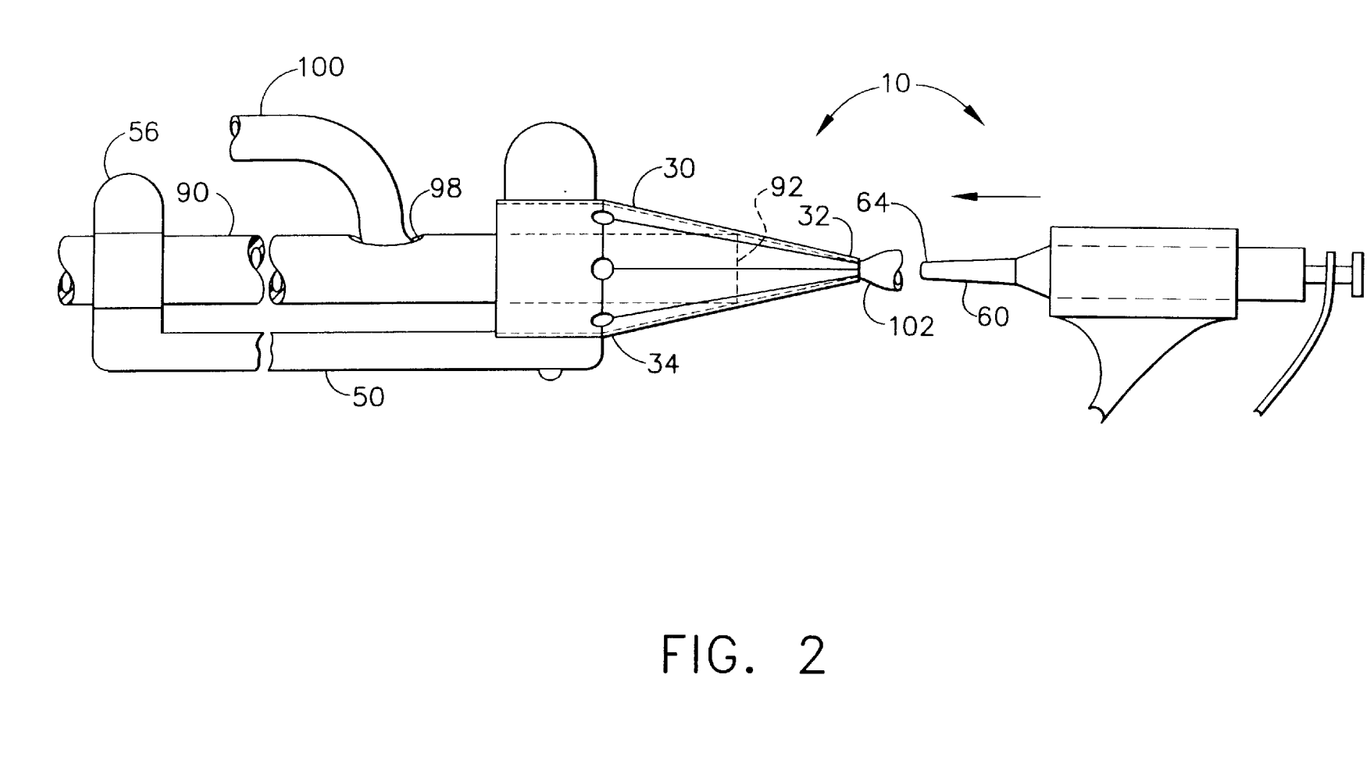
FIG. 2 is a side view of eversion instrument 10 of FIG. 1, including a conical holder 30, illustrated holding a vessel 100 as a mandrel 60 is aligned for insertion into vessel 100.

Referring first of all to FIG. 1, an eversion instrument 10 of the present invention is seen adjacent to a tubular workpiece 90, also referred to as a tube 90. Referring also to FIG. 2, a side view of eversion instrument 10 is illustrated mounted onto tube 90, which contains a vessel 100. Vessel 100 may be a blood vessel, such as a segment of the greater saphenous vein having a diameter of about 2–8 mm. The present invention, however, may be adapted for eversion of other hollow organs of the body. Tube 90 has a proximal end 94 and a distal end 97 and represents numerous kinds of bushings, ferrules, tubes, and specialized devices having an approximately cylindrical shape with an axial bore. The operator, an assistant, or a mechanical holding device holds tube 90 as the operator uses eversion instrument 10 to evert (i.e., turn inside out) a vessel portion 102 of vessel 100 onto a distal end 92 of tube 90.

As shown in FIG. 1, eversion instrument 10 comprises a frame 50 having a proximal end 54 and a distal end 52. A conical holder 30, also referred to as a cone 30, is attached to distal end 52. A proximal spring clip 56 is attached to proximal end 54. In this embodiment, proximal spring clip 56 and cone 30 are sized to snap onto tube 90, so that frame axis 58 is coaxial with tube axis 97, and slides longitudinally along tube 90. Eversion instrument 10 further comprises a mandrel 60 springably retained in a bushing 86 attached to a distal end 84 of a handle 80.

Figure 3:
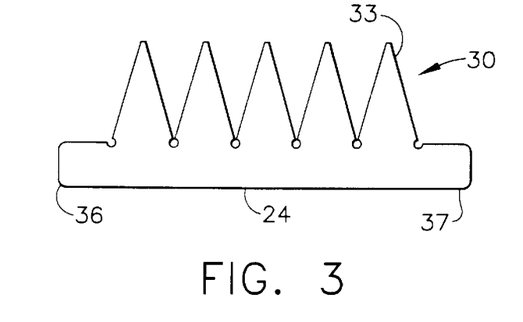
FIG. 3 is a plan view of conical holder 30 shown in a flattened or unraveled configuration.
Figure 4:
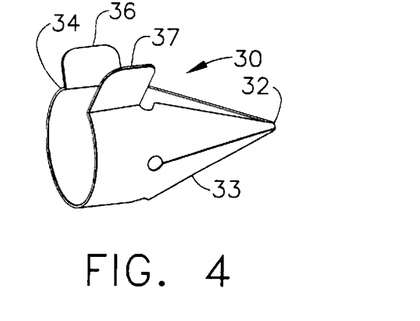
FIG. 4 is a perspective view of conical holder 30, shown in a funnel shaped configuration.

Cone 30 includes a distal end 32 and a proximal end 34. When unconstrained, cone 30 normally has a conical shape with distal end 32 having a smaller diameter (for the present embodiment, for example, in the range of 1–3 mm) than the diameter of proximal end 34. Cone 30 is preferably made from a rigid material with spring properties such as stainless steel sheet having a thickness approximately in the range of 0.1 to 0.5 mm. FIG. 3 shows a plan view of cone 30 when in a flattened configuration as it may be cut from a flat sheet of material. A plurality of flutes 33 extend from a rail portion 24, which has a first end 36 and a second end 37. When formed into a funnel shape as shown in FIG. 4, flutes 33 converge to define distal end 32 and are expandable to a diameter greater than that of tube 90 shown in FIG. 1. First end 36 and second end 37 are flared as shown to facilitate mounting around tube 90 and removal from tube 90. Proximal end 34 has a diameter that is larger than that of tube 90, so that when cone 30 is mounted over tube 90 as shown in FIG. 2, distal end 92 of tube 90 contacts the inside of cone 30 about midway between distal end 32 and proximal end 34 of cone 30. Those skilled in the art will recognize that cone 30 may also be designed to be injection molded from a rigid plastic, such as polycarbonate, directly into a funnel shape.

Figure 5:
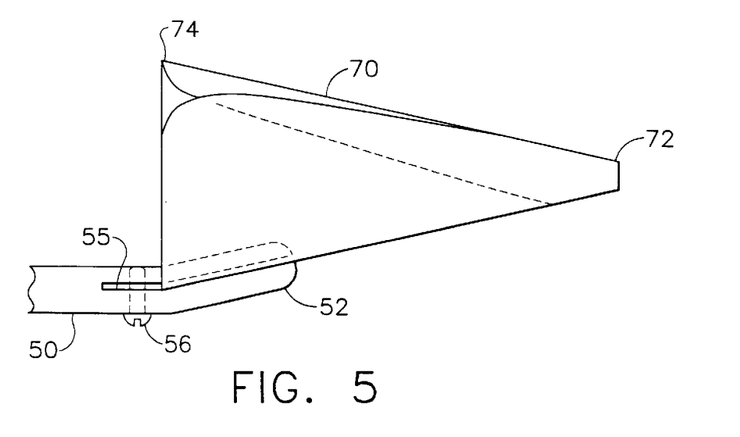
FIG. 5 is a side view of an alternate embodiment of a conical holder 70 of eversion instrument 10 shown in FIG. 1, with conical holder 70 mounted in a frame 50.
Figure 6:
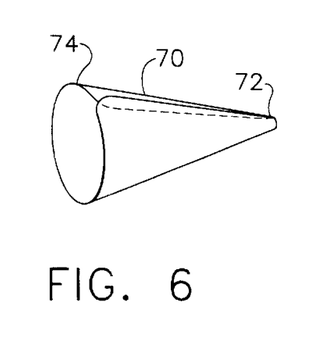
FIG. 6 is a perspective view of conical holder 70 shown in a funnel shaped configuration.
Figure 7:
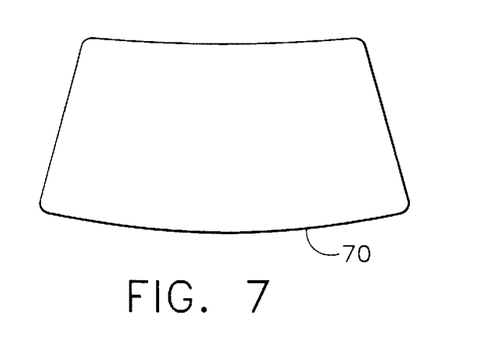
FIG. 7 is a plan view of conical holder 70 shown in a flattened or unraveled configuration.

FIG. 5 shows an alternate embodiment of the present invention in which a cone 70 comprises a rolled sheet of a stiff but resilient material including but not limited to, for example, any one the following: approximately 0.25 mm thick cellulose acetate propionate (CAP), approximately 0.25 mm thick polycarbonate (PC), and approximately 0.10 mm thick stainless steel foil (shimstock). Cone 70 is made preferably of a transparent material such as clear PC or clear CAP for visualization of vessel 100 during the eversion method steps. One method for constructing cone 70 from PC or CAP sheet is to cut a flat piece using a pattern (see FIG. 7), roll the flat piece into a funnel shape (see FIG. 6) and place in a holding fixture, place the fixture in an oven that is set at the material deflection temperature (about 280 F. for PC; 192 F. for CAP) for about 1–2 minutes to soften the material, and then permit the fixture and material to cool to room temperature before removing the cone from the fixture. Cone 70 is attached to frame 50 in a slot 55 on distal end 52 of frame 50, with a screw fastener 56 tightened to close slot 55 onto proximal end 74 of cone 70. The diameters of proximal end 74 and distal end 72 of cone 70 are approximately the same as for cone 30 in the previous embodiment shown in FIG. 4.

Referring again to FIG. 1, eversion instrument 10 further comprises a leaf spring 110 having a proximal end 112 attached with a pair of fasteners 114 to proximal end 82 of handle 80. A distal end 114 of leaf spring 110 is retained in a turned-down portion 61 of a proximal end 66 of mandrel 60, to springably bias mandrel 60 in a distal (left) direction. Mandrel 60 slides freely in an axial bore 88 of bushing 86. A distal end 64 of mandrel 60 inserts into vessel 100 during the eversion method. Spring 110 deflects at a predetermined sufficiently effective force in the range of, for example, approximately 0.2 to 1.0 N, and limits the maximal insertion force of mandrel 60 into tube 90, thus helping to prevent injury to vessel 100.

FIG. 2 and FIGS. 8 through 13 illustrated steps of a procedure for using eversion instrument 10 to evert a vessel end 102 of vessel 100 over distal end 92 of tube 90.

Referring to FIG. 2, the operator inserts vessel 100 through a side opening 98 of tube 90 and through the axial bore of tube 90 until vessel end 102 extends out the distal end 92 of tube 90. A suture filament (not shown) temporarily attached to the end of vessel 100 facilitates passing vessel 100 through tube 90. The operator pulls vessel end 102 through distal end 32 of cone 30 until the desired length necessary for eversion is obtained. The operator next aligns distal end 64 of mandrel 60 with vessel end 102.

Figure 8:
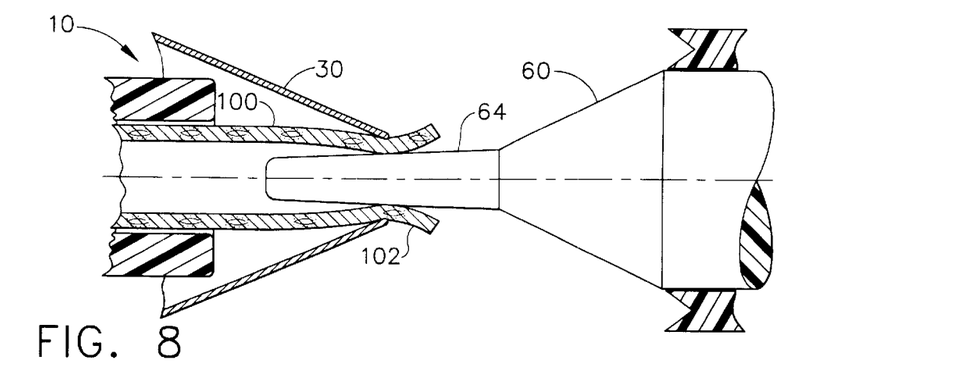
FIG. 8 is a partial side cross-sectional view of eversion instrument 10 illustrating a step of inserting mandrel 60 into a vessel 100.
Figure 9:
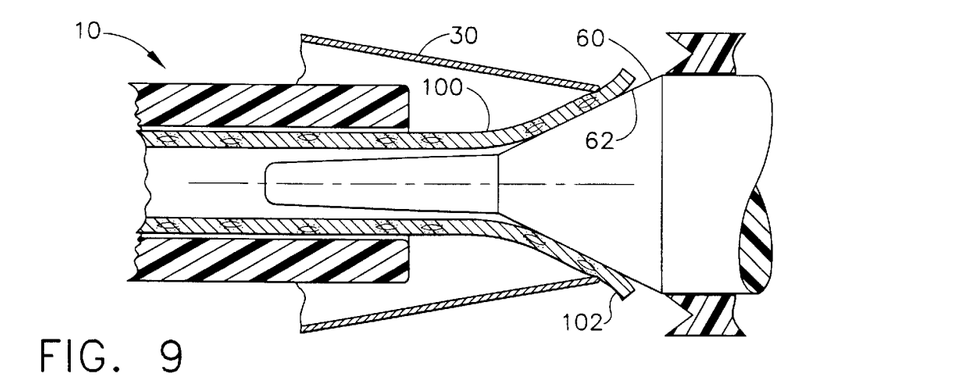
FIG. 9 is a partial side cross-sectional view of eversion instrument 10 illustrating a step of dilating vessel 100 onto a tapered portion 62 of mandrel 60.
Figure 10:
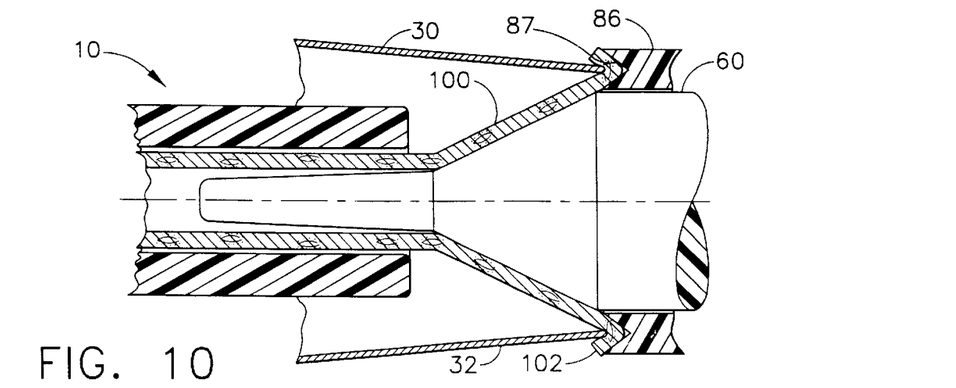
FIG. 10 is a partial side cross-sectional view of eversion instrument 10 illustrating a step of engaging a circumferential edge 106 of vessel 100.
Figure 11:
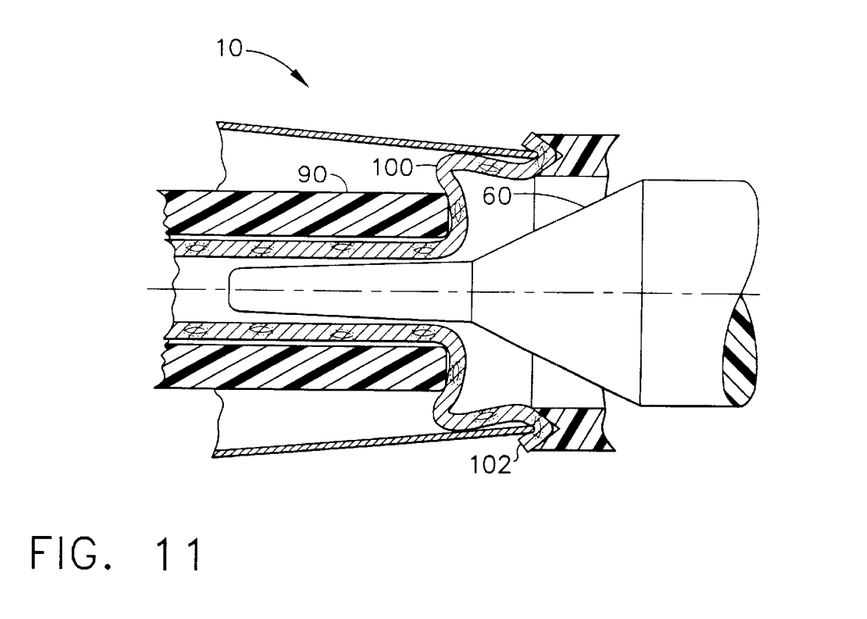
FIG. 11 is a partial side cross-sectional view of eversion instrument 10 illustrating a step of everting vessel 100 onto tube 90.
Figure 12:
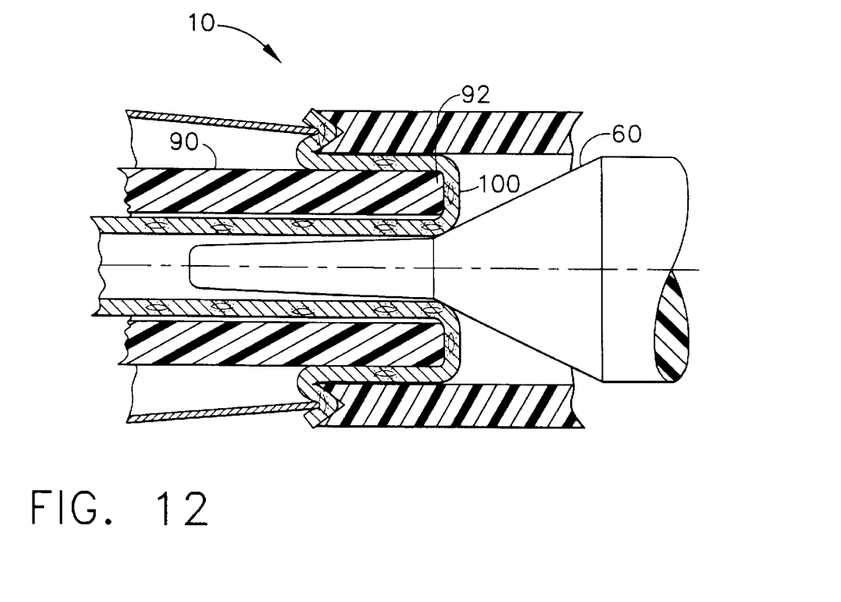
FIG. 12 is a partial side cross-sectional view of eversion instrument 10 illustrating the end of the step of everting vessel 100 onto tube 90.
Figure 13:
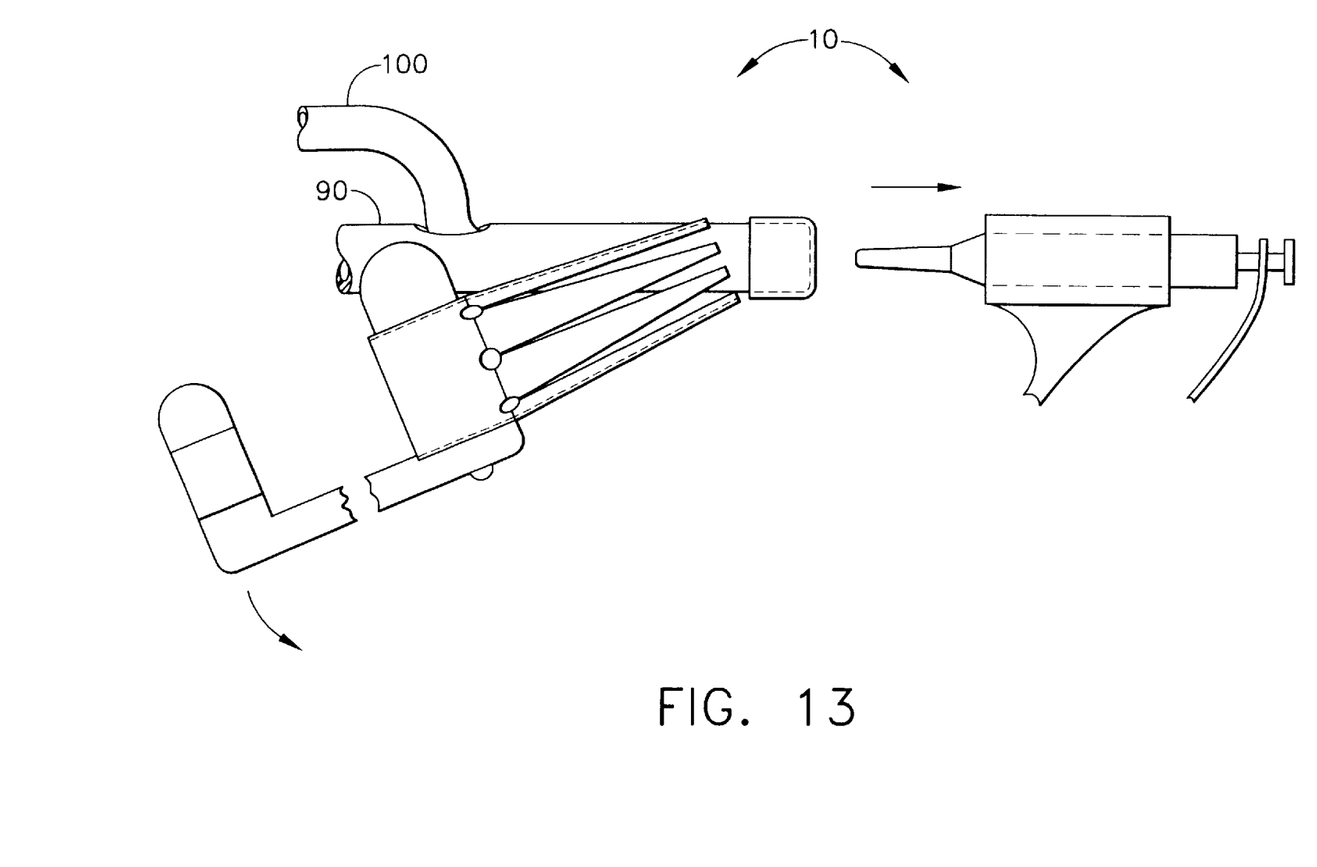
FIG. 13 is a side view of eversion instrument 10 shown during the step of removing eversion instrument 10 from tube 90 after eversion of vessel 100.

Now turning to FIG. 8, the operator inserts distal end 64 of mandrel 60 into the lumen of vessel end 102 of vessel 100. Cone 30 expands radially to hold vessel 100 securely against distal end 64. The operator then further inserts mandrel 60 into vessel 100 as shown in FIG. 9, so that vessel end 102 rides up a tapered portion 62 of mandrel 60, and vessel end 102 dilates. The operator further advances mandrel 60 towards cone 30 as shown in FIG. 10. Distal end 32 of cone 30 expands radially so that vessel end 102 is engaged, or pinched, between distal end 32 of cone 30 and an annular groove 87 on bushing 86. As the operator continues to advance mandrel 60 and bushing 86 toward tube 90 as shown in FIGS. 11 and 12, cone 30 is caused to slide proximally with respect to tube 90 as vessel 100 is pulled over the distal end 92 of tube 90. In FIG. 12, mandrel 60 is shown abutting vessel 100 against distal end 92 of tube 90. As noted earlier, leaf spring 110 (see FIG. 1) limits the allowable insertion force of mandrel 60 into tube 90. FIG. 13 shows the removal of eversion instrument 10 from tube 90, which still contains everted vessel 100.

Eversion instrument 10 as described for the specific embodiments shown in FIGS. 1–13 is easily constructed from low cost plastics and/or metals and may be supplied to the end user as a sterilized unit intended for single patient use. A re-sterilizable embodiment of eversion instrument 10, intended for multi-patient use, however, will become apparent to those skilled in the art. Also, eversion instrument 10 may be made available in a variety of sizes to accommodate a wide range of sizes and types of bodily hollow organs, adaptable to eversion onto various kinds of tubular workpieces.

EXAMPLE

A patient undergoing cardiac coronary artery bypass graft (CABG) surgery is prepared for surgery and anesthetized in a conventional manner in accordance with the prevailing medical standards. The patient's chest is opened in a conventional manner by cutting through the sternum and expanding the rib cage with a conventional surgical retractor instrument. The patient's heart is accessed in a conventional manner and the patient is connected to a pulmonary bypass machine and the heart is stopped. A section of the patient's saphenous vein, which has already been harvested by this time, is prepared for use as a graft vessel. The graft vessel end that is to be attached to the aorta for the proximal anastomosis is everted using an eversion instrument of the present invention as already described in the detailed description and shown in FIGS. 2 and 8–13. In FIG. 13, vessel 100 is shown everted over distal end 92 of tube 90. One embodiment of tube 90 is disclosed in published patent application WO0056228, "Low Profile Anastomosis Connector", filed on Mar. 20, 2000, assigned to By-Pass, Inc., and which is hereby incorporated herein by reference. As described in WO0056228, a metallic anastomosis connector comprising a plurality of ring segments is used to fasten the graft vessel to another vessel such as the aorta. The distal end of the graft vessel is then anastomotically attached to a coronary artery on the heart using a conventional hand suturing method. Additional bypasses are performed in the same manner or variations, depending on the patient's condition and anatomy. The remainder of the CABG procedure is conducted in a conventional manner and includes the steps of inspecting and repairing the grafts for leaks, checking blood flow, removing the patient from the pulmonary bypass machine, and closing the surgical incision.

The eversion instruments and eversion methods of the present invention have many advantages. The present invention is less traumatic to the intima of the vessel during the eversion procedure than conventional surgical graspers and the like. The present invention is easy for the surgeon to use without assistance and requires only a few steps to operate. The present invention is useful for a wide range of blood vessel sizes, particularly small vessels, e.g., having a diameter of about 2–3 mm or less. In addition, the present invention is useful on one end of a vessel, when the opposite end is already attached to the patient (e.g., at the distal anastomosis of a patient undergoing a CABG procedure). The present invention also allows for the proper length of everted tissue over the tube, bushing, or the like, depending on the requirements of the anastomosis device or method being used. Finally, the present invention may be manufactured inexpensively.

Accordingly, there is a need in this art for novel devices and methods for engaging and everting the end of a blood vessel (or other tubular body organ) over a member such as a tube, ferrule, bushing, or the like which can be used in a quick and effective manner without causing trauma to the vessel or the intima of the vessel (or tubular body organ).

Although this invention has been shown and described with respect to detailed embodiments thereof, it will be understood by those skilled in the art that various changes in form and detail thereof may be made without departing from the spirit and scope of the claimed invention.

What is claimed is:

1. An instrument for everting an end of a vessel, comprising:

a conical holder member having a first end, a second end, a longitudinal axis, and a lumen therethrough, said conical holder member positionable coaxially with a tubular member, said tubular member comprising an axial bore, a proximal end, a distal end and an outer surface, said distal end of said tubular member having a diameter, said lumen of said conical holder member at said first end having a first diameter smaller than the diameter of the distal end of the tubular member when positioned distal to the distal end of the tubular member, said first end radially expandable so that said lumen at said first end can have an expanded diameter larger than the diameter of the distal end of the tubular member;

a mandrel having a first end, a second end, and a longitudinal axis therebetween, said first end of said mandrel insertable into said first end of said conical holder member, said mandrel tapered from a smaller diameter at said distal end to a larger diameter at said proximal end; and, a sleeve having an axial sleeve bore for slidably retaining said mandrel in coaxial alignment with said longitudinal axis of said conical holder, said sleeve having a distal end, wherein said distal end has an annular groove for pressing against said first end of said conical holder member with a section of vessel located therebetween.

2. The instrument of claim 1, wherein the conical holder member comprises a plurality of fluted members, each member having a distal free end and a proximal fixed end, wherein the proximal fixed end is fixedly mounted to an annular member.

3. The instrument of claim 1 additionally comprising a longitudinal frame member mounted to the conical member.

4. The instrument of claim 3, additionally comprising a spring retention member mounted to the frame for engaging the tubular member.

5. The instrument of claim 3, additionally comprising a spring retention member mounted to the frame for engaging the tubular member.

6. The instrument of claim 1 additionally comprising a handle mounted to the sleeve.

7. The instrument of claim 6, additionally comprising a leaf spring having a first end mounted to the handle and a second end mounted to the proximal end of the mandrel.

8. The instrument of claim 1 wherein the conical member is slidably mounted over the tubular workpiece.

9. The instrument of claim 1 wherein the conical member can be opened to remove it laterally from the tubular member.

10. The instrument of claim 1, wherein the tubular member comprises a tube wall, and a hole through the tube wall in communication with the axial bore.

11. The combination comprising:
   I. a tubular member comprising a distal end, a proximal end, an outer surface and an axial bore; and,
   II. an instrument for everting an end of a vessel, comprising:
      a conical holder member having a first end, a second end, a longitudinal axis, and a lumen therethrough, said conical holder member positionable coaxially with a tubular member, said tubular member comprising an axial bore, a proximal end, a distal end and an outer surface, said distal end of said tubular member having a diameter, said lumen of said conical holder member at said first end having a first diameter smaller than the diameter of the distal end of the tubular member when positioned distal to the distal end of the tubular member, said first end radially expandable so that said lumen at said first end can have an expanded diameter larger than the diameter of the distal end of the tubular member;
      a mandrel having a first end, a second end, and a longitudinal axis therebetween, said first end of said mandrel insertable into said first end of said conical holder member, said mandrel tapered from a smaller diameter at said distal end to a larger diameter at said proximal end; and,
      a sleeve having an axial sleeve bore for slidably retaining said mandrel in coaxial alignment with said longitudinal axis of said conical holder, said sleeve having a distal end, wherein said distal end has an annular groove for pressing against said first end of said conical holder member with a section of vessel located therebetween.

12. The combination of claim 11, wherein the conical holder member comprises a plurality of fluted members, each member having a distal free end and a proximal fixed end, wherein the proximal fixed end is fixedly mounted to an annular member.

13. The combination of claim 12 wherein the instrument additionally comprises a longitudinal frame member mounted to the conical member.

14. The combination of claim 13 wherein the conical member can be opened to remove it laterally from the tubular member.

15. The combination of claim 12 wherein the instrument additionally comprises a handle mounted to the sleeve.

16. The combination of claim 15 wherein the instrument, additionally comprises a leaf spring having a first end mounted to the handle and a second end mounted to the proximal end of the mandrel.

17. The instrument of claim 12 wherein the conical member is slidably mounted over the tubular workpiece.

18. The combination of claim 11, wherein the tubular member comprises a tube wall, and a hole through the tube wall in communication with the axial bore.

19. A method for everting the end of a vessel, comprising the steps of:
   providing a tubular member, said tubular member comprising a distal end, a proximal end, an outer surface and an axial bore;
   providing an instrument for everting an end of a vessel, comprising:
      a conical holder member having a first end, a second end, a longitudinal axis, and a lumen therethrough, said conical holder member positionable coaxially with a tubular member, said tubular member comprising an axial bore, a proximal end, a distal end and an outer surface, said distal end of said tubular member having a diameter, said lumen of said conical holder member at said first end having a first diameter smaller than the diameter of the distal end of the tubular member when positioned distal to the distal end of the tubular member, said first end radially expandable so that said lumen at said first end can have an expanded diameter larger;
      a mandrel having a first end, a second end, and a longitudinal axis therebetween, said first end of said mandrel insertable into said first end of said conical holder member, said mandrel tapered from a smaller diameter at said distal end to a larger diameter at said proximal end; and,
      a sleeve having an axial sleeve bore for slidably retaining said mandrel in coaxial alignment with said longitudinal axis of said conical holder, said sleeve having a distal end, wherein said distal end has an annular groove for pressing against said first end of said conical holder member with a section of vessel located therebetween;
   inserting a blood vessel into the axial bore of the tubular member such that a distal end of the blood vessel extends out from the distal end of the tubular member and out from the distal end of the conical member;
   inserting the first end of the mandrel into the distal end of the blood vessel and the first end of the conical member;
   moving the mandrel and sleeve axially toward the tubular member and such that the first end of the mandrel moves into the axial bore of the tubular member and the sleeve engages the distal end of the blood vessel; and,
   moving the conical member proximally with respect to the tubular member,
   thereby everting the distal end of the blood vessel over the distal end of the tubular member.

* * * * *